United States Patent [19]
Mackert et al.

[11] Patent Number: 4,541,801
[45] Date of Patent: Sep. 17, 1985

[54] COLOR SCALE PALETTE

[75] Inventors: Wilhelm Mackert, Rodenbach; Karlheinz Matthay, Oberursel, both of Fed. Rep. of Germany

[73] Assignee: Kulzer & Co. GmbH, Wehrheim, Fed. Rep. of Germany

[21] Appl. No.: 599,937

[22] Filed: Apr. 13, 1984

[30] Foreign Application Priority Data

Oct. 12, 1983 [DE] Fed. Rep. of Germany ....... 8329441

[51] Int. Cl.⁴ ............................................. A61C 19/10
[52] U.S. Cl. ...................................................... 433/26
[58] Field of Search ........................................... 433/26

[56] References Cited

U.S. PATENT DOCUMENTS 2,765,534 10/1956 Bloom et al. .......................... 433/26
4,115,922 9/1978 Alderman ............................. 433/26

Primary Examiner—Robert Peshock
Attorney, Agent, or Firm—Felfe & Lynch

[57] ABSTRACT

A color scale palette has color sample rods tinted all along their lengths from a stem in a frame to the other end projecting from the frame. The frame has a window for exposing a portion of the color sample rods and, for example, a color key, and studs cooperative with a bore through the stem end of each color sample rod for snapping it into the frame. The bore is preferably a funnel-shaped for shadow-free as well as juxtaposed color comparisons.

20 Claims, 2 Drawing Figures

COLOR SCALE PALETTE

BACKGROUND OF THE INVENTION

The invention relates to a color scale palette and, more particularly, one for the identification and selection of a dental material.

As used herein, the term "dental material" is to be understood to refer to dental filling materials, prosphetic detal materials for the preparation of dental plates, manufactured teeth and tooth parts, and the like.

German patent publication No. G 1,714,429 discloses a color scale palette in the form of a plastic stick arranged to hold removable color rods in a row as color samples. For this, the stick has recesses which removably accommodate the color rods. For use in selecting the color of a dental material, therefore, several color rods which appear from general inspection to be most suitable could be identified first, and these color rods then removed from the stick for more-exacting selection. For example, in selecting the color for a manufactured tooth to be inserted in a person's mouth between other teeth, the color rods generally appearing most suitable in relation to the color or colors of the other teeth could be selected first, and these then removed from the stick for selecting the best one by juxtaposed comparison with the other teeth.

This procedure seems simple, but is, instead, complex for reasons relating both to the problems of color selection and to the color scale palette used for the selection. Color selection is difficult because the preception of color is variable and, even once perceived, the selection of the most suitable color is artistically esoteric. These problems are particularly acute in relation to dental materials.

The dental materials and the natural or other mouth structures with which the dental materials are to be used are often translucent and, in situ, moist. The translucence and the gloss of the moisture affect the appearance of color. The color for dental materials is usually selected indoors where artificial light is used, but the color of the dental materials, once in place in a person's mouth, must also appear appropriate when the person is out doors. The dental materials are also used in very close proximity to natural or other mouth structures so that correspondingly close precision in color selection is required. Shadows compound these problems because the intensity of the light and its angle in assessing the color affect the appearance of the color to be selected. Finally, at least natural mouth structures are not one color, but many, and vary widely from person to person, so that neither mere mechanical selection nor reference to standard pre-selected colors is a satisfactory substitute for individual artistic selection.

All these problems are compounded by the difficulty of satisfying each individual who is to receive the dental material not only with the color finally selected, but with the cost of making the selection and, of course, implementing it.

In relation to the color scale palette, these problems mean that the color scale items, the color rods of the above-referenced patent publication, must be shaded precisely and, hence, sufficiently large and numerous. They must not fall from their holder during initial selection, yet be removable for juxtaposed comparisons under both artificial and natural light and returnable to the palette easily to allow both accurate and efficient selection. Further, it would be desirable to have the color scale items (rods) coded as to color identification and/or dental material(s) for implementing the color selected and arranged to avoid shadows at least in the juxtaposed comparison.

SUMMARY OF THE INVENTION

It is, therefore, an object of the invention to create a color scale palette for the identification and selection of a dental material, particularly, which, on the one hand, will provide a secure mounting for the color samples on a palette frame but, on the other hand, will also permit easy removal of the samples from the palette frame and thus simplify and promote the use of the color scale palette.

This and other objects are accomplished by the invention. A color scale palette frame removably receives color samples in such a way that they both project from the frame and are visible through a window in the frame. This exposes as much of each color sample as possible while the samples are in the frame for easier initial identification and selection of the samples before they are removed for more-precise, juxtaposed comparison. A stud on the frame snaps into a recess on a stem of ezch color sample when the color sample is in the frame to keep the color samples from falling out of the frame during the initial selection. The recess is preferably a funnel-shaped, through bore to allow shadow-free juxtaposed comparison of the color sample with another color, for example of a tooth, when the color sample is un-snapped and removed from the frame. The side of the frame opposite the window is preferably cut away in a way to facilitate such removal.

BRIEF DESCRIPTION OF THE DRAWING

A preferred embodiment of the color scale palette which is intended to illustrate but not to limit the invention will now be described with reference to drawings thereof in which.

DESCRIPTION OF A PREFERRED EMBODIMENT

Figure 1:
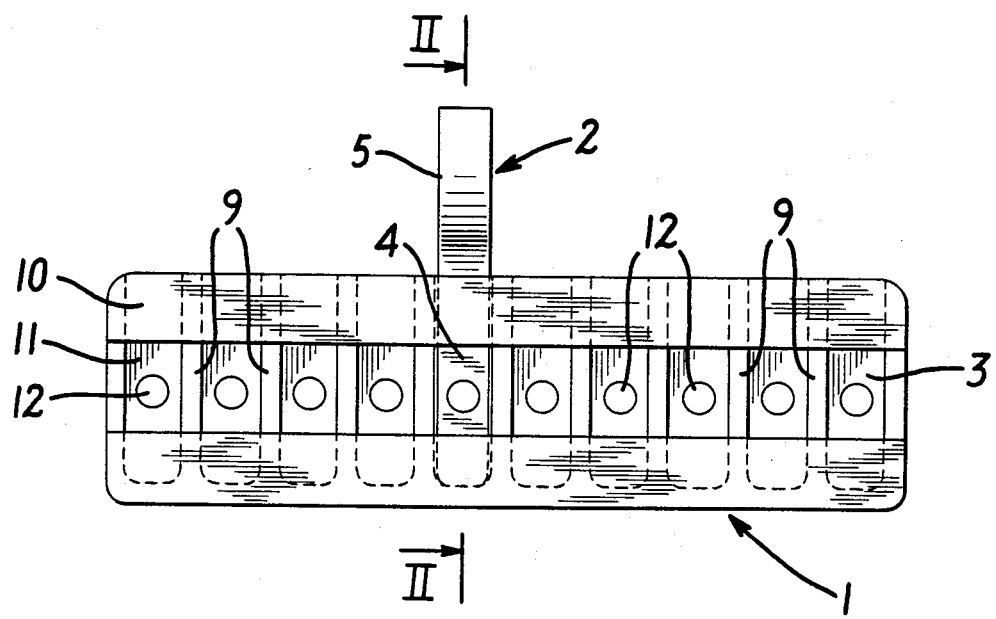
FIG. 1 shows a top view of the preferred embodiment.

The color scale palette shown in FIG. 1 is in the form of a color scale stick. It has a palette frame 1 in which color samples in the form of rods 2 are mounted in a sample row, preferably according to a scale of tints.

The palette frame 1 has a window 3 in one side over each color rod 2 in the frame. This window displays characteristics, keys or codes 12 on a stem 4 of each color rod 2 as well as more of its color when the rods are in the frame 1. The characteristics, keys or codes are, for example, the manufacturer's identification of dental material to be selected with the palette.

Figure 2:
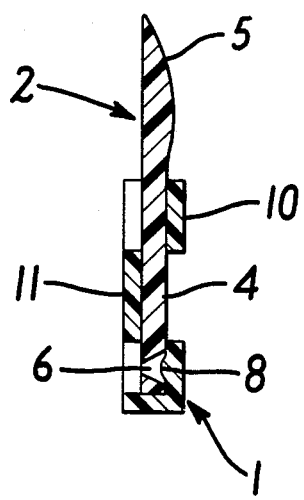
FIG. 2 shows a cross section through the preferred embodiment of FIG. 1.

As seen in FIG. 2, each color rod 2 is one piece, preferably a plastic injection molding. Each is tinted, for example to match a color of a dental material, all along its length. The free end 5 of each color rod which projects from the palette frame 1 when the rod is in the frame is made of greater thickness than the stem 4 to facilitate the withdrawal of the color rod from the palette frame. Furthermore, the thickening of the end assures easier judgment of color for, for example, the intended, exacting identification and selection of a dental material color.

As FIG. 2 also indicates, the stem 4 of each color rod has a recess 6 which, in this preferred embodiment, is a through-bore for snap-engaging a stud or cam 8 on the palette frame 1 when the stem is fully mounted therein. The advantage of forming the recess 6 as the bore shown is for identifying the color of a dental material better by placing the tinted stem against the tooth or the gum the color of which is to be matched with the color of a dental material selected with the rod. The color can then be compared all around the perimeter of the bore.

In this preferred embodiment, the bore 6 is also funnel-shaped with the larger hole diameter intended to be cooperative with the stud 8 for more easily releasing the rod from the frame. In the color identification, the smaller hole diameter is also placed directly on the tooth or gum, thus avoiding shadows in the color matching operation.

Returning to the frame 1, it has a guide 9 between each pair of color rods 2 and at the ends for guiding the color rods into the palette frame. The guides 9 also spacedly connect a cover plate 10 defining the window 3 centrally thereacross and carrying the studs 8 on the side thereof opposite that from which the ends 5 of the color rods 2 project and a back plate 11 for holding the rods against the cover and, especially, the stud. The back plate corresponds in size and position with the window 3, both extending all across the frame 1, to facilitate removing and inserting the rods. The multiple guides 9 thus also make the frame 1 strong, rigid, and durable even though its plates 10, 11 are cut away for the window and ease of rod insertion. The rigidity cooperates with the stud 8 and recess 6 arrangement for releasably holding the rods 2 in the frame because flexure of the frame could inadvertently release the color rods.

The frame 1 of the color scale palette is advantageously made entirely of plastic by injection molding. Both the palette frame 1 and the rods 2 for the color samples with their stems are thus, respectively, single plastic pieces.

What is claimed is:

1. A color scale palette, especially for selecting a dental material, comprising:
   color rods each being tinted a different color all along its length and having a bore through one, stem end for color comparision therethrough; and
   a frame for removably receiving the stem end of each color rod with the other ends of the rods projecting from the frame, the frame having guides, cover and back plates spacedly connected to each other by the guides between each pair of the color rods for, together, guiding the stem ends of the color rods into the frame with the other ends of the color rods projecting from the frame, and a stud which snaps into the bore through the stem end of each color rod when so guided into the frame.

2. The color scale palette of claim 1, and further comprising window means in the frame for exposing a portion of the stem end of each color rod when in the frame.

3. The color scale palette of claim 2, wherein the other end of each color rod is thicker than its stem end.

4. The color scale palette of claim 2, wherein the bore is funnel-shaped.

5. The color scale palette of claim 2, wherein the window means comprises a window centrally across the cover plate, the studs being on a side thereof opposite that from which the other ends of the color rods project from the frame, and the back plate corresponds in size and position with the window.

6. The color scale palette of claim 1, and further comprising an identifying characteristic on a portion of the stem of each color rod and window means in the frame for exposing the portion of the stem of each color rod when in the frame.

7. The color scale palette of claim 6, wherein the other end of each color rod is thicker than its stem end.

8. The color scale palette of claim 6, wherein the bore is funnel-shaped.

9. The color scale palette of claim 6, wherein the window means comprises a window centrally across the cover plate, the studs being on a side thereof opposite that from which the other ends of the color rods project from the frame, and the back plate corresponds in size and position with the window.

10. The color scale palette of claim 6, wherein at least portion of the stem of each color rod is the same color as the end thereof.

11. The color scale palette of claim 6, wherein the end of each color rod is thicker than its stem.

12. The color scale palette of claim 10, wherein the recess comprises a funnel-shaped bore through the stem of each color rod.

13. The color scale palette of claim 11, wherein the recess comprises a funnel-shaped bore through the stem of each color rod.

14. The color scale palette of claim 10, wherein the window means comprises a window centrally across the cover plate, the studs being on a side thereof opposite that from which the ends of the color rods project from the frame, and the back plate corresponds in size and position with the window.

15. The color scale palette of claim 13, wherein the window means comprises a window centrally across the cover plate, the studs being on a side thereof opposite that from which the ends of the color rods project from the frame, and the backplate corresponds in size and position with the window.

16. The color scale palette of claim 1, wherein the end of each color rod is thicker than its stem.

17. The color scale palette of claim 16, wherein the recess comprises a funnel-shaped bore through the stem of each color rod.

18. The color scale palette of claim 16, wherein the window means comprises a window centrally across the cover plate, the studs being on a side thereof opposite that from which the ends of the color rods project from the frame, and the back plate corresponds in size and position with the window.

19. The color scale palette of claim 1, wherein the recess comprises a funnel-shaped bore through the stem of each color rod.

20. The color scale palette of claim 19, wherein the window means comprises a window centrally across the cover plate, the studs being on a side thereof opposite that from which the ends of the color rods project from the frame, and the back plate corresponds in size and position with the window.

UNITED STATES PATENT AND TRADEMARK OFFICE
CERTIFICATE OF CORRECTION

PATENT NO. : 4,541,801

DATED : September 17, 1985

INVENTOR(S) : Wilhelm Mackert et al.

It is certified that error appears in the above-identified patent and that said Letters Patent is hereby corrected as shown below:

Column 1, lines 9-10, "prosphetic" should be -- prosthetic --.

Column 2, line 24, "ezch" should be -- each --.

Column 3, line 26, after "plate" insert -- 11 --.

Claims 10 and 12, cancel claims

Claim 13, line 2, change "recess comprises a" to -- bore is --.

Claim 13, lines 2-3, delete "bore through the stem of each color rod".

Claim 14, line 1, change "10" to -- 11 --.

Claim 14, line 4, before "ends" insert -- other --.

Claim 15, line 4, before "ends" insert -- other --.

UNITED STATES PATENT AND TRADEMARK OFFICE
CERTIFICATE OF CORRECTION

PATENT NO. : 4,541,801

DATED : September 17, 1985

INVENTOR(S) : Wilhelm Mackert et al.

It is certified that error appears in the above-identified patent and that said Letters Patent is hereby corrected as shown below:

Claim 15, line 5, change "backplate" to -- back plate --, before "end" insert -- other --.

Claim 16, line 2, after "stem" insert -- end --.

Claim 17, line 2, change "recess comprises a" to -- bore is --.

Claim 17, lines 2-3, delete "bore through the stem of each color rod --.

Claim 18, cancel claim.

Claim 19, line 2, change "recess comprises a" to -- bore is --.

Claim 19, lines 2-3, delete "bore through the stem of each color rod."

Claim 20, cancel claim.

Signed and Sealed this

Twenty-second Day of April 1986

[SEAL]

Attest:

DONALD J. QUIGG

Attesting Officer

Commissioner of Patents and Trademarks